United States Patent
Johansson et al.

(12)

(10) Patent No.: US 6,428,524 B1
(45) Date of Patent: *Aug. 6, 2002

(54) PANTY-TYPE SANITARY NAPKIN

(75) Inventors: Kerstin Johansson, Ulricehamn; Roy Hansson, Mölndal; Ann Samuelsson, Lindome, all of (SE)

(73) Assignee: SCA Hygiene Products AB, Gothenburg (SE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 555 days.

(21) Appl. No.: 08/817,573
(22) PCT Filed: Nov. 6, 1995
(86) PCT No.: PCT/SE95/01312
  § 371 (c)(1),
  (2), (4) Date: Apr. 23, 1997
(87) PCT Pub. No.: WO96/14039
  PCT Pub. Date: May 17, 1996

(30) Foreign Application Priority Data

Nov. 8, 1994 (SE) .............................................. 9403832

(51) Int. Cl.[7] .......................... A61F 13/15; A61F 13/20
(52) U.S. Cl. ..................................... 604/385.3; 604/396
(58) Field of Search .......................... 604/385.1, 385.2, 604/393, 394, 391, 385.01, 385.24–385.3, 385.22

(56) References Cited

U.S. PATENT DOCUMENTS

| 4,337,771 A | * | 7/1982 | Pieniak et al. ............ 604/385.2 |
| 4,560,381 A | | 12/1985 | Southwell |
| 5,135,522 A | * | 8/1992 | Fahrentrug et al. ....... 604/385.2 |
| 5,500,063 A | * | 3/1996 | Jessup ...................... 604/385.2 |
| 5,545,158 A | * | 8/1996 | Jessup ...................... 604/385.2 |
| 5,569,234 A | * | 10/1996 | Buell et al. .............. 604/385.2 |
| 5,624,420 A | * | 4/1997 | Bridges et al. ........... 604/385.2 |

FOREIGN PATENT DOCUMENTS

| EP | 0 323 634 | 12/1988 | |
| GB | 0744690 | 2/1953 | |
| GB | 1198902 | 1/1969 | |
| GB | 2236939 | 9/1990 | |
| GB | 2 244 422 | 12/1991 | |
| JP | 4371147 | * 12/1992 | .............. 604/385.2 |
| JP | 4371148 | * 12/1992 | .............. 604/385.2 |
| SE | 500 791 | 4/1991 | |
| WO | 92/03113 | 3/1992 | |
| WO | 95/09592 | 4/1995 | |

OTHER PUBLICATIONS

Translation of JP 4–371147, Nov. 1997.*
Translation of JP 4–371148, Nov. 1997.*

* cited by examiner

Primary Examiner—John G. Weiss
Assistant Examiner—K. M. Reichle
(74) Attorney, Agent, or Firm—Burns, Doane, Swecker & Mathis, L.L.P.

(57) ABSTRACT

A pants-type sanitary napkin or incontinence guard for women including a front part, a back part and an intermediate crotch part. An elastically stretchable waist border includes first and second side parts and central parts disposed therebetween. The opposing side edges of the front part and the back part are joined together by the first and second side parts of the waist border. The elasticized waist border has a greater resistance to stretch in the first and second side parts than in the central parts thereof, when no load is acting on the sanitary napkin or guard.

9 Claims, 2 Drawing Sheets

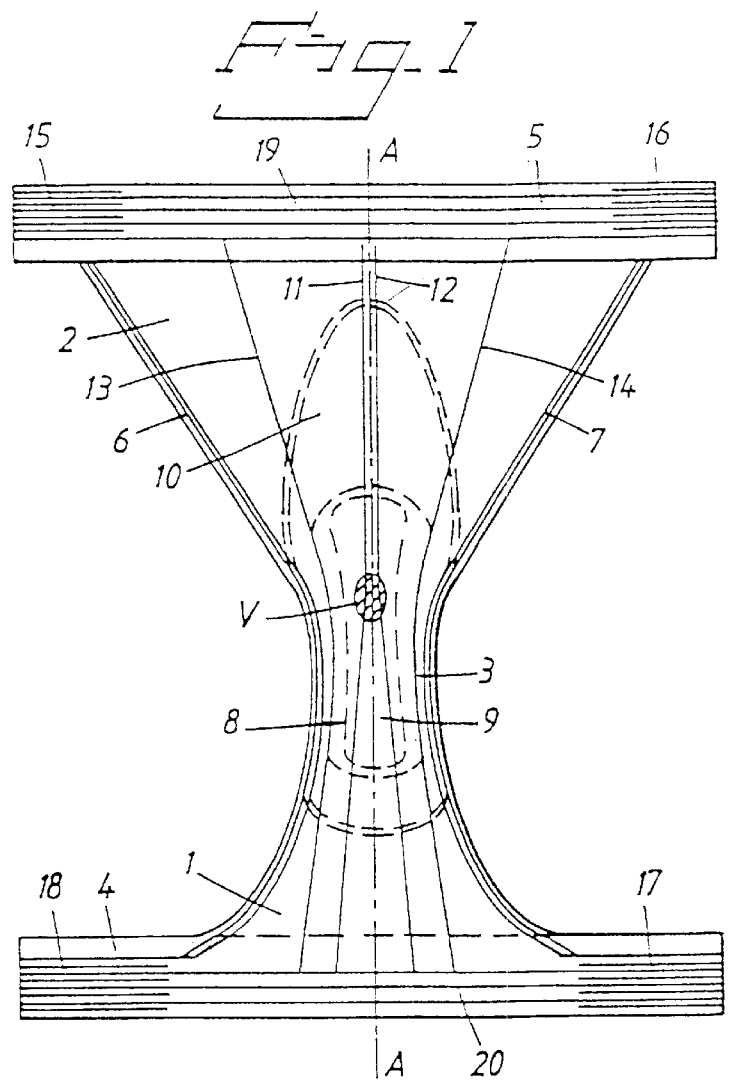
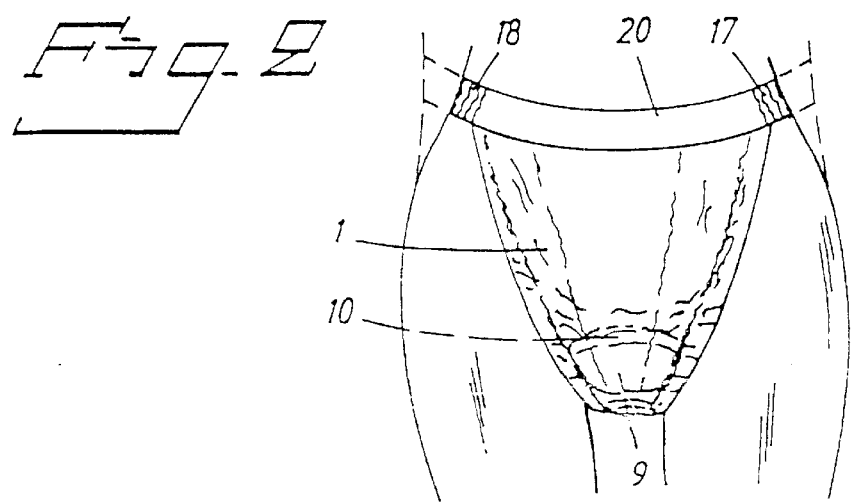

PANTY-TYPE SANITARY NAPKIN

TECHNICAL FIELD

The present invention relates to a panty-type sanitary napkin or an incontinence guard for women, comprising a front part, a back part and an intermediate crotch part, wherein opposing side parts of the front and back parts are joined together, and which further comprises an elastically stretchable waist border or edge which extends peripherally around the free end-edges of the front and back napkin parts.

BACKGROUND OF THE INVENTION

The reason why sanitary napkins leak is often because the absorbent body of the napkin is not initially positioned correctly, or because the absorbent body is moved out of its correct position while in use. It is therefore very important that the panty-napkin combination fits well on the wearer, if reliability against leakage is to be achieved. In the case of panty-type sanitary napkins, i.e. panties having an integrated absorbent body, the absorbent body will be positioned correctly when putting on the napkin, provided that the napkin properly fits the wearer. However, the shapes of the bodies of women who use pants-type sanitary napkins vary greatly. For instance, the waist measurements of some wearers will vary while having the same buttock sizes, depending on whether the wearer has a straight figure or a more pronounced female shape with broad hips and a narrow waist. Consequently, it is difficult to produce pants-type sanitary napkins in a model or a size which will ensure a good fit on users of all sizes. Another problem with poorly fitting napkins is that the folds and wrinkles caused by contraction of the elastic in the packaged state of the napkin are not smoothed out when putting on the napkin. These folds and wrinkles can be seen through the overlying garments of thin or slender users, thereby causing the user embarrassment.

SUMMARY OF THE INVENTION

The object of the present invention is to solve these problems. This object is achieved in accordance with the invention with a pants-type sanitary napkin or an incontinence guard for women of the kind defined in the introduction which is characterized in that when the napkin is free of load, the waist border will have a greater resistance to stretch in those parts of the border that are located in the side parts than in remaining parts. Thus, those parts of the waist border which have a lower stretch resistance will be stretched first, while those parts which have a greater stretch resistance will only be stretched when necessary. It is therewith possible to ensure a good fit for both users who have a straight figure and those who have broad hips and narrow waists. One advantage afforded in this regard is that fewer models or sizes need be produced in order to accommodate variations in the body shapes of the users while providing a good and snug fit.

According to one preferred embodiment of the pants-type sanitary napkin, the elastic waist border has the form of an elastic band or tape which is fastened while in a stretched state to the free end-edges of the front and back napkin parts. The parts of the elastic band or tape which are located in the side parts of the napkin have a stronger elasticity, or exert a greater elastic strength, than the remainder of the band, and the mutually opposing side edges of the front and back napkin parts are spaced from one another and joined together through band parts of stronger elasticity. The band may advantageously be comprised of a two-layer material which includes one elastic layer and one layer of non-elastic material, said layers being mutually joined in a more sparse bonding pattern in those parts of the band that are located in the side parts of the front and back napkin parts than in the remainder of the band. Alternatively, the band may be comprised of two different materials each having a different elastic strength or degree of elasticity.

According to a second embodiment, the waist elastic is comprised of a plurality of elastic threads which are fastened to the free edges of the front and back napkin parts with the threads in a pre-stretched state, wherein a larger number of threads are mounted in the side parts of the front and back napkin parts than in the remainder of the napkin.

According to a third embodiment of the invention, the side parts of the front and back napkin parts are spaced from on another and mutually joined by means of an elastically stretchable band, while the remainder of the waist border or edge has a much lower degree of elastic stretchability than the elastic stretchability of the band.

BRIEF DESCRIPTION OF THE DRAWINGS

The invention will now be described with reference to the accompanying drawings, in which FIG. 1 illustrates from above a preferred embodiment of an inventive pants-type sanitary napkin, and shows the napkin in a final stage of manufacture prior to joining the front and back napkin parts together;

FIG. 2 is a front view of the napkin shown in FIG. 1 worn by a user, after having joined the front and back parts together;

DETAILED DESCRIPTION OF THE PREFERRED EMBODIMENTS

Figure 3:
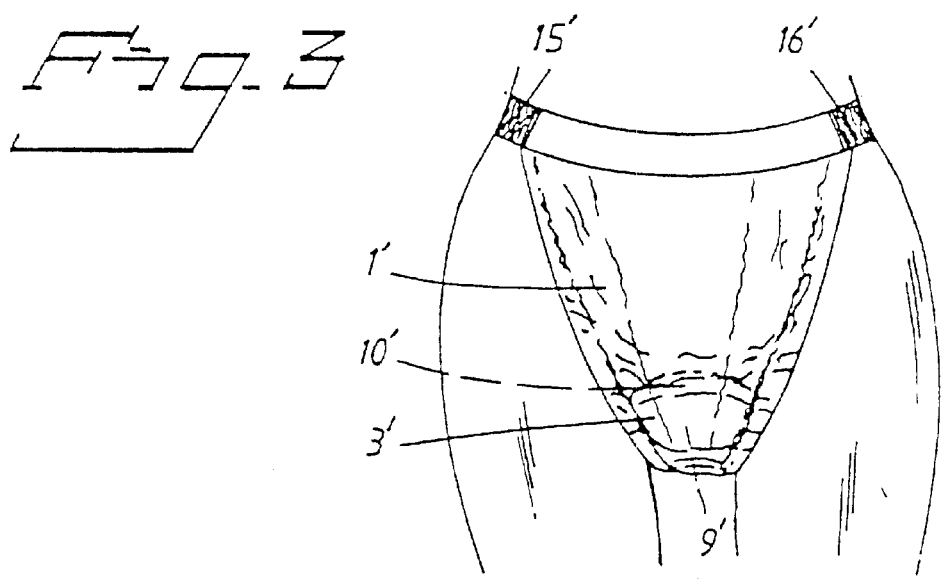
FIG. 3 is a view similar to FIG. 2 and shows a second embodiment of an inventive pants-type sanitary napkin.

FIG. 1 illustrates one embodiment of a pair of inventive sanitary panties or pants-type sanitary napkin in a stage of manufacture prior to joining together the front and back waist parts of the napkin. The illustrated napkin includes a front part 1, a back part 2 and an intermediate crotch part 3. The napkin also includes waist elastic which in the illustrated case is comprised of elastic bands 4, 5 which extends along respective edges of the waist-forming parts of the front and the back napkin parts, and also includes leg elastic in the form of elastic threads 6, 7 which extend along the side edges of the napkin between the elastic bands 4, 5. In the case of the illustrated embodiment, two elastic threads are disposed along each side edge of the napkin, although it will be understood that the leg elastic may instead consist in fewer or more threads, or in elastic tape, bands or the like. The Figure also shows in broken lines an absorbent body 8 which is firmly secured to the napkin. The illustrated absorbent body 8 is comprised of a primary absorbent pad 9 and a secondary absorbent pad 10 and is particularly suited for night wear.

The illustrated napkin is also provided with two elastic threads 11, 12 which extend between the elastic bands 4 and 5 of the front and back napkin parts 1, 2 respectively, symmetrically in relation to a central longitudinal line A-A along the napkin. The threads 11, 12 extend from the waist edge or rear edge of the back part 2 parallel with the longitudinal line of the napkin, and in close proximity of one another, up to a region V in the crotch part 3. The region V is located at the center of the user's crotch when the napkin is worn. The threads 11, 12 thereafter diverge from the region V and continue to the waist edge or front edge-of the front napkin part 1.

When using a pants-type sanitary napkin constructed in accordance with the embodiment shown in FIG. 1, the parts of the threads 11, 12 that diverge away from the region V will strive to give the absorbent body 8 a basin-like shape within this region, this basin-like shape conforming well with the anatomy of the wearer in said region. The parts of the threads 11, 12, that extend rearwardly and parallel with one another from the region V strive to press a corresponding central part of the absorbent body in between the buttocks of the wearer when the napkin is in use, thereby bringing the absorbent body into positive abutment with the wearer's body, at least within the crotch part and at the beginning of the back napkin part, therewith making the napkin safe against leakage from the rear of the napkin.

The napkin illustrated in FIG. 1 also includes elastic threads 13, 14 which are located laterally outside the threads 11, 12 and which extend between the front and the back napkin parts, wherein the threads in the front part are mutually convergent and the threads in the back part are mutually divergent. These threads also follow the outer contours of the sides of the primary absorbent pad 9 along a greater part of their longitudinal extension. The threads 13, 14 thus ensure that the side edges of the primary absorbent pad will be pressed into tight abutment with the user's body, and will also assist in ensuring that the secondary absorbent pad will conform to the shape of the user's body. It should be mentioned in this regard that the secondary absorbent pad is thin and very flexible and is intended to provide an additional safety zone for absorbing any leakage that may occur when the absorbent body is used over a long period, for when the napkin is worn overnight and the absorbent capacity of the secondary absorbent pad is therefore relatively small.

The absorbent body used with the illustrated pants-type sanitary napkin is fastened to the napkin in the manufacturing stage illustrated in FIG. 1, in which the aforedescribed elastic elements are in a stretched state. When manufacture of the napkin is complete, the elastic elements will strive to contract to a tensionless state. This results in the formation of folds or pleats in those regions of the napkin which lie outside the primary absorbent pad 9, and the threads will contract in these regions to an essentially tensionless state. This contraction of the napkin is counteracted by the primary absorbent pad 9 within the region of said pad, to a greater or a lesser extent depending upon the stiffness of the pad. Present-day thin absorbent bodies are very flexible and will therefore be folded or pleated by the elastic threads, although full contraction of the threads is prevented. Thus, when the user puts on the napkin, any folds or wrinkles in the absorbent pad 9 will be smoothed out and the pad will lie in abutment with the wearer's body as a result of the elastic force exerted by the threads 11–14. Because of the wearer's anatomy, the absorbent pad 9 will obtain a concave basin-like shape from the region V and forwardly thereof, therewith causing the contraction force exerted by the threads 11–14 in this region to strive to retain the basin-like shape, while those parts of the absorbent pad 9 which lie along the threads will be pressed into sealing abutment with the wearer's body. The parallel parts of the elastic threads 11, 12 also ensure that the part of the absorbent pad 9 which lies rearwardly of the region V will be deformed so as to conform to the anatomy of the user in this region, so that the part of the absorbent body or pad that lies between the user's buttocks will be in sealing abutment with the user's body. In addition to ensuring that the side edges of the absorbent pad 9 will lie in sealing abutment with the wearer's body, the threads 13, 14 also function to prevent folds or bulges from forming in the napkin or in the secondary absorbent pad.

The pants-type sanitary napkin illustrated in FIG. 1 is preferably comprised of two layers, which are joined together in some suitable way, for instance by gluing, and the elastic devices are disposed between these layers and fastened thereto by gluing or by welding with ultrasound or by heat-welding. The elastic devices may also be sewn to the napkin.

As before mentioned, the absorbent body 8 illustrated in FIG. 1 is comprised of a primary and a secondary absorbent pad 9 and 10 respectively. The primary absorbent pad 9 is constructed in the same way as a conventional absorbent body of a sanitary napkin and therefore has an absorption capacity which is sufficient to handle the fluid discharged by the wearer over the time period for which the napkin is intended to be used, for instance over a whole night. The absorbent body or pad may, for instance, comprise one or more layers of compressed cellulose fluff with or without an admixture of superabsorbent material. The primary absorbent pad 9 may advantageously comprise one or more layers of roll material, i.e. absorbent material which has been pre-compressed and treated so as to enable the material to be rolled onto storage reels. Such absorbent pads may be very thin and highly flexible while still having sufficient absorption capacity for use as a night napkin. The secondary absorbent pad 10 has a much larger extension than the primary pad and extends rearwardly over a large part of the back part of the napkin. The primary purpose of the secondary absorbent pad is to enhance security against leakage and the pad will have a given absorption capacity commensurate with this purpose. To this end, the secondary pad may be comprised of tissue, nonwoven or some other roll material. The secondary absorbent pad 10 will also preferably include means for preventing fluid, liquid, from spreading over the surface of the pad. Such barriers may be obtained, for instance, by pleating or creping the material layer, or with the aid of barrier welds. The use of nonwoven material which includes fibres of so-called superabsorbent material is also conceivable, this material binding the absorbed liquid chemically. However, the secondary absorbent pad will generally have the same flexibility as the material from which the napkin is made, so as to make the napkin comfortable to wear. The secondary absorbent pad must therefore be very thin and will consequently have a highly limited absorption capacity.

The absorbent body 8 comprised of the primary and the secondary absorbent pads is enclosed conventionally between a liquid permeable casing sheet and a liquid-impermeable, conveniently air-permeable, backing sheet which, in use, lies against the panty part of the napkin.

The aforedescribed pants-type sanitary napkin is constructed in accordance with Swedish Patent Application No. 9303284-5. In order for the napkin to function in the intended manner when used, it is essential that the waist elastics 4, 5 are able to hold the napkin in place on the wearer. Furthermore, it is essential to the aforesaid functions of the elastic threads 11–14 that the front and the back napkin parts are stretched laterally when putting on the napkin.

To ensure this, the waist elastics 4, 5 have different degrees of elasticity, or different elastic strengths, in different parts thereof. This is achieved in the FIG. 1 embodiment by virtue of providing the elastic waist bands 4, 5 with more pre-stretched elastic threads in the side parts 15–18 of said elastic than in the central parts 19, 20 thereof. As a result, the side parts will have a greater resistance to stretch than the remaining parts of the waist elastic. Thus, when putting on the pants-type sanitary napkin shown in FIG. 1, the central parts 19, 20 will be stretched first while the side parts 15–18 will only be stretched when the central parts of said elastic have been stretched to an extent at which the combined elastic strength of the outwardly stretched threads in the central parts 19, 20 is equal to the combined elastic strength of the threads in the side parts 15–18. This ensures that the front and back napkin parts will be stretched in the manner intended before any appreciable stretching of the side parts 15–18 of the waist elastic 4, 5 takes place. Any folds or creases in the front and back napkin parts will also be smoothed out in this way.

FIG. 2 illustrates schematically the pants-type napkin shown in FIG. 1 when worn by a user. Certain parts of the body contours of a user having broad hips and a narrow waist are shown in full lines. As indicated in the Figure, the central parts 19, 20 of the waist elastic are almost stretched to the full, whereas the side parts 15–18 have only been stretched to an insignificant extent. The broken lines in FIG. 2 are intended to show the body contours of a user whose bottom is of the same width as the first-mentioned user, but who has a straight figure. The additional stretch in the waist elastic required for a user of this shape is achieved through the medium of the side parts 15–18 of the elastic.

In the case of the aforedescribed embodiment, it is only the stretch resistance of the side parts that differs from the stretch resistance of the remainder of the waist elastic. It will be understood, however, that it is also possible to vary the stretch resistance in other parts of the waist elastic, for instance so that the elastic in the front part of the napkin will be stretched before the elastic in the back part thereof, or so that the stretch resistance will decrease continually towards the centre part of the waist elastic in the front and/or back part of the napkin.

In the described embodiment, the different degrees of elasticity, or elastic strength, in different parts of the waist elastic has been achieved by mounting a different number of elastic threads of one and the same kind in different parts of the border elastic 4, 5. It will be understood, however, that the different degrees of elasticity can be achieved in other ways, for instance by using elastic threads of mutually different spring characteristics in different parts of the waist elastic or to compose the waist elastic of different elastic materials.

Figure 4:
FIG. 4 is a schematic perspective view of one side part of the napkin shown in FIG. 3.

FIGS. 3 and 4 illustrate a second embodiment of an inventive pants-type sanitary napkin in which the stretch resistance of the side parts of the waist elastic is twice that of an elastic which is comprised of the same material, this being achieved by virtue of using doubled elastic material in said side parts. Such waist elastic can be used with particular benefit in a pants-type sanitary napkin, which is normally manufactured by placing the napkin components on a moving, flat web of material, wherein the individual napkin blanks are cut from the web in a final stage of manufacture and the side parts of the blank cut-outs are joined together to form the finished pants-type napkin. The desired higher stretch resistance in the side parts of the waist elastic can be achieved readily by giving those parts of the waist elastic that extend out from the front and back parts of the napkin dimensions which will cause the outwardly projecting parts to overlap when joining the waist elastic in the side parts and therewith joining the pants-type napkin together in its entirety. The napkin shown in FIG. 3 differs from the napkin shown in FIGS. 1 and 2 solely by the different construction of the side parts. Those reference signs used in FIGS. 1 and 2 have been used in FIGS. 3 and 4 with the addition of a prime to identify corresponding components. FIG. 4 illustrates one side part of the pants-type napkin and also shows that the parts 15', 18' have been overlapped when joining the napkin together. Naturally, in order for the overlapped parts 15', 18' of the waist elastic to function as an elastic unit, it is necessary to join both ends of the overlapped parts together, for instance by means of a weld join 21, 22 at each end. In addition to affording the advantage of a greater stretch resistance in the mutually overlapping parts of the elasticated waist border, it will also afford the advantage of a strong and aesthetically attractive join in the side parts of the pants-type sanitary napkin. The opposite side part of the napkin is constructed in the same manner.

The waist elastic used in a pants-type sanitary napkin according to the invention may also have the form of the elastic band taught by SE-B-500 791. That is, as described therein, the elastic band or tape includes a first layer of elastic material and a second layer of material which is practically inelastic in comparison with the first layer. The side edges of the front and the back napkin parts are spaced apart and joined together by means of the elastically stretchable band such that the central part of the waist elastic has insignificant elastic stretchability in comparison with the elastic stretchability of the band. Different degrees of elasticity or elastic strengths are obtained in different parts of the band, by joining the two layers together in different bonding patterns. More particularly, the layers are joined together in a sparser bonding pattern in those parts of the bond that are located in the side parts of the front and the back napkin parts than in the remainder of the band.

It will be understood that the invention can also be applied with pants-type sanitary napkins of a type different to those described in the exemplifying embodiments, for instance of the type in which the waist elastic includes elastic threads which are fastened to the outer casing sheets and which do not include the separate elastic bands included in the illustrated embodiments, or in pants-type sanitary napkins in which the side edges of the front and the back napkin parts are joined directly one to the other. Even though it is unnecessary from the aspect of leakage safety or absorption for the front and back napkin parts to extend laterally outwards, the user feels that the napkin fits more snugly when the napkin includes such a feature, which is important from the comfort aspect. The invention is therefore restricted solely by the content of the following claims.

What is claimed is:

1. A sanitary napkin or incontinence guard for women, comprising:
    a front napkin part having a free end-edge including opposing side edges,
    a back napkin part having a free end-edge including opposing side edges,
    an intermediate crotch part, and
    an elastically stretchable waist border or edge which extends peripherally around the free end-edges of the front and the back napkin parts, said waist border having first and second side parts and central parts disposed therebetween, the opposing side edges of the front napkin part and the back napkin part being joined together by said first and second side parts of the waist border,
    wherein, when no load acts on the napkin or guard, the elasticized waist border has a greater resistance to stretch in the first and second side parts thereof than in the central parts.

2. The napkin according to claim 1, wherein the elastic waist border or edge is made from an elastic band or tape which is fastened in a stretched state to the free end-edges of the front and back napkin parts, the elastic band or tape including a first side part and a second side part having a greater elastic strength than central parts of the elastic band or tape, said first side, second side, and central parts of said elastic band or tape corresponding to said first side, second side, and central parts of said waist border or edge, respectively.

3. The napkin according to claim 2, wherein the opposing side edges of the front and back napkin parts are spaced apart and joined together through the medium of said first and second side parts of the elastic band.

4. The napkin according to claim 2, wherein the band is comprised of two layers of material, one of said layers being an elastic layer and the other said layer being an essentially non-elastic layer, the layers are joined together in a sparser bonding pattern in the side parts of the band than in the central parts of said band.

5. The napkin according to claim 2, wherein the band is comprised of two different materials having mutually different elastic strengths.

6. The napkin according to claim 1, wherein the elastic waist border includes a plurality of elastic threads which are fastened in a pre-stretched state to the free edges of the front and back napkin parts, the side parts of the elastic waist border having a larger number of threads than the central parts of the elastic waist border.

7. The napkin according to claim 1, wherein the side edges of the front and the back napkin parts are spaced apart and joined together by means of the side parts of the waist border which each comprise an elastically stretchable band; and in that central parts of the elastic waist border or edge has insignificant elastic stretchability in comparison with the elastic stretchabilities of the bands.

8. A napkin according to claim 1, wherein the side parts of the waist border or edge include a projecting part projecting out from each side edge of the back and front napkin parts and the projecting parts of each side edge of the back napkin part and a corresponding one of the projecting parts of each side edge of the front napkin part overlap one another and are joined together along a join line at an end of each projecting part.

9. The napkin of claim 1, wherein the waist border includes a first waist border portion extending peripherally around the free end-edge of the front napkin part and a second waist border portion extending peripherally around the free end-edge of the back napkin part, each said waist border portion having opposing first and second side parts and a central part disposed therebetween, and said first and second side parts of the first waist border portion being joined with respective first and second side parts of the second waist border portion, said first side, second side, and central parts of said waist border portions corresponding to said first side, second side, and central parts of said waist border or edge, respectively.

* * * * *